United States Patent [19]

Hanus

[11] 4,240,413

[45] Dec. 23, 1980

[54] ERECTION HOLDER

[75] Inventor: Judith Hanus, Cham, Switzerland

[73] Assignee: Francois W. Gasser, Bern, Switzerland

[21] Appl. No.: 23,850

[22] Filed: Mar. 21, 1979

[51] Int. Cl.³ .............................................. A61F 5/00
[52] U.S. Cl. ..................................................... 128/79
[58] Field of Search .................................. 128/79, 346

[56]         References Cited
         U.S. PATENT DOCUMENTS

| 2,705,951 | 4/1955 | Crowner | 128/79 |
| 3,455,301 | 7/1969 | Clark | 128/79 |
| 3,621,840 | 11/1971 | Macchioni | 128/79 |
| 3,626,931 | 12/1971 | Bysakh | 128/79 |

FOREIGN PATENT DOCUMENTS 554178  7/1932  Fed. Rep. of Germany ............. 128/79

*Primary Examiner*—Lawrence W. Trapp
*Attorney, Agent, or Firm*—Blair, Brown & Kreten

[57]         ABSTRACT

An erection holder to enable or prolong an erection of the penis of a man. It has a body of sleeve-like configuration with an outer sleeve wall surface, a hollow interior surrounded by an inner sleeve wall surface, a base end destined for coming to rest, during use, against a portion of the user's abdomen, surrounding the root of his penis, and an outer end. Openings are in the base end and the inner end. A first inwardly directed protrusion surrounds the opening in the base end and a second inwardly directed protrusion surrounds the opening in the outer end. A circumferential lip portion extends from the base end in an axial direction and is preferably integral with the body of the holder and preferably forms a circumferential blunt edge with the said first protrusion. Between the two protrusions the sidewall of the body is outwardly curved and preferably barrel-shaped.

8 Claims, 3 Drawing Figures

ERECTION HOLDER

BACKGROUND OF THE INVENTION

This invention relates to an erection holder as means for making possible or prolonging the erection of the penis, in particular for substantially impotent men or men of weak sexual potency.

The coitus which leads both partners to have an orgasm and find full satisfaction is of the greatest importance for the psychic and physical equilibrium of a human being. It is particularly important for each man so as to strengthen and preserve his self-confidence, that he is assured of being able to satisfy his wife sexually and make her happy at all times.

The modern way of life in which situations of stress recur with great frequency cause an ever larger number of men to lack at an increasing number of occasions the ability to carry out a satisfying coitus. A direct consequence thereof is lack of potency or complete impotence, carrying with them a well known negative influence on the relationship between husband and wife.

These problems are well known, and there have been repeated attempts to devise and market auxiliary means which remedy or overcome an insufficient or completely failing erectability of the penis. A great variety of partial or total protheses are known which, however, are all either inconvenient to use or unesthetic or both. As only one example, there is mentioned the German Offenlegungs-Schrift No. 24 60 812 of Leonhard Schmid, dated July 1st, 1976.

Moreover, erection holders are known which consist of an elastic sleeve of a length of about 5 centimeters. The shape of this sleeve is substantially cylindrical, and its base end which is destined to enclose the penis at its root is stiffer than its opposite end which is directed away from the body of the user. The greater stiffness of the body near end region of the sleeve is either provided by a greater thickness of the sleeve wall or by using for this region a material of higher elasticity modulus. Moreover, the sleeve may bear radially extending protrusions. An erection holder of this type has been described in U.S. Pat. No. 3,455,301 to Clark.

The purpose of using this type of device is to produce a damming up, or congestion, of the blood in the penis, the elastic sleeve serving as a type of blood-damming valve. For obvious reasons of health, the passage of blood through the veins extending from the body of the user into the penis must not be completely interrupted and it is very difficult to attain a desired optimal congestion effect. For this reason, the last-mentioned U.S. Patent mentions expressly that the cylindrical sleeve must be most easily deformable at its outer end, whereby it is widened when axial pressures occur during use.

Thereby, the inner width of the sleeve is periodically narrowed toward the base end thereof, and the temporary increases in the congestion effect caused thereby are destined to compensate for the undesirable effects of the aforesaid axial pressures.

However, in practice the known devices of this type achieve a completely reliable result only when all of the relevant factors, and in particular the required deformation force at determined regions as well as the inner diameter of the sleeve are very closely adapted to the physiological factors and conditions of the user. This results in the need for a large number of types of a great variety of dimensions which complicates their manufacture and renders it costly. At the same time it becomes difficult for the user to choose the type most suited for him.

OBJECTS AND SUMMARY OF THE INVENTION

It is, therefore, an object of the invention to provide an erection holder which is so devised that it fits users in a wide range of the above-mentioned physiological factors and conditions while offering a reliable satisfactory effect within that wide range, thus considerably reducing the number of types of erection holders required to satisfy the widest number of users, and thereby also effectively reducing costs of manufacture.

It is another object of the invention to provide an erection holder which is free from the drawbacks of the known types thereof, and which is simple, offers an aesthetic aspect and is safe to use.

It is yet another object of the invention to provide an erection holder which brings the penis to full erection rapidly and which holds the penis in erected condition for a prolonged time also after ejaculation has taken place while assisting automatically in exciting the clitoris of the woman in a natural manner.

A further object of the invention is to provide an erection holder which is pleasant in use for both partners and does not disturb either of them during the coitus; which is odorless or of neutral odor, which can be used repeatedly, and which is chemically inert to the excretions of both partners.

These objects are attained according to the invention in an erection holder of the above-mentioned sleeve type consisting of an elastic material of determined extensibility and bearing inwardly directed radial protrusions on the inner sleeve wall, the base region of which sleeve has a higher resistance to deformation than the outer end thereof, wherein a first radial protrusion which is destined to surround a penis at its root bears a substantially axially extending circumferential lip portion, and herein a second inwardly directed circumferential radial protrusion is located away from said first radial protrusion toward or at the outer end of the said sleeve, while the wall portion of the sleeve between the first and the second radial protrusion is of an outwardly convex barrel configuration, whereby the inner width of the sleeve is enlarged toward the central region of said portion, thus providing a damming-up zone intermediate said first and second protrusion.

Preferably, the first radial protrusion is of a larger diameter, in untensioned condition, less extensibility and/or flexibility, than the afore-mentioned second radial protrusion, while the region of the sleeve wall intermediate the two protrusions has a minimum resistance to deformation.

It is also preferred that the first radial protrusion is provided with an inwardly directed blunt circumferential edge, where the base end of the sleeve merges with the inner convexly vaulted inner wall of the circumferential lip portion. A radius of 3 to 6 millions of the curvature of the first radial projection on the side of the said edge facing away from the lip portion in an axial sleeve section is preferred. The erection holder according to the invention which preferably covers about one quarter to one half, optionally about one third of the length of the penis, has a blood flow-congesting effect, the first and second protrusions acting as blood-damming valves of different congesting strength, while the lip portion of the sleeve acts at the root of the penis as a suction means. This is achieved by the fact that the lip becomes sufficiently thinner toward its circumferential outer edge so that it can expand to be turned outwardly away from the central longitudinal axis of the holder body.

It is advantageous to manufacture the erection holder of the invention when the latter is of axially symmetrical configuration, and is preferably shaped as a small barrel, open at both ends. It should be manufactured from an elastomeric material which is non-injurious to health, preferably odorless or of pleasant inoffensive odor, and soft and preferably smooth. This material may optionally contain antibacterial substances. Its color is preferably that of the skin of potential users. Suitable elastomers are, for instance, silicone rubber and especially soft natural or synthetic rubber, such as butyl caoutchouc, which should preferably be free from biologically or chemically active constituents and, of course, free from any adjuvants having an irritating effect on the skin or micoins membranes of the partners, such as vulcanizations accelerators (curing agents).

Furthermore, polymers and copolymers of vinyl chloride, vinylidene chloride, or acrylonitrile, polyester amides or polyurethanes which are plasticized with plasticizers that are neither injurious to health nor irritating are suitable as materials for the manufacture of erection holders according to the invention.

While the above-mentioned materials are preferred, other elastomers having the above described properties can likewise be used.

BRIEF DESCRIPTION OF THE DRAWINGS

Further details of the erection holder according to the invention are explained in the following description of a preferred embodiment thereof in conjunction with the drawings in which.

DETAILED DESCRIPTION OF THE ILLUSTRATED EMBODIMENT

Figure 1:
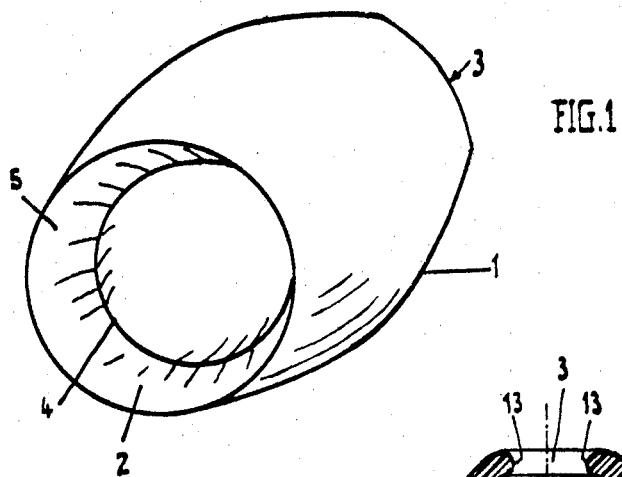
FIG. 1 shows the preferred embodiment in perspective.

The erection holder in FIG. 1 is of barrel-shaped configuration and has an outer barrel-wall surface 1, a base end opening 2, an outer end opening 3, of smaller diameter than opening 2 a first inwardly directed protrusion 4, and a lip portion 5 extending beyond opening 2 and surrounding the latter. The outer surface of the lip portion 5 merges smoothly with the surface 1 so as to form an integral part of the latter.

Figure 2:
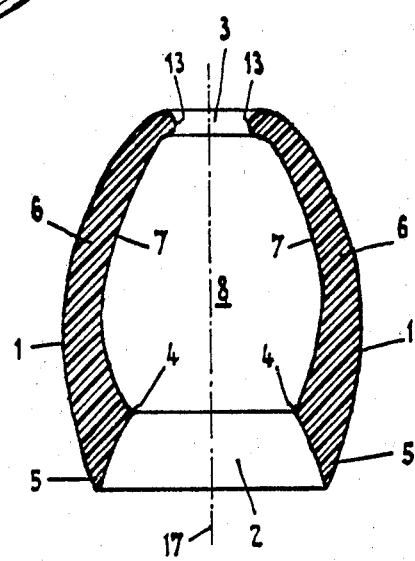
FIG. 2 is an axial sectional view of the embodiment.

The barrel wall 6 of the erection holder has its outer surface 1 extending substantially parallel to the inner sidewall 7 of the holder especially in the middle region between openings 2 and 3, as shown in FIG. 2. The hollow interior 8 of the holder thus acts as a congestion space for the amount of blood in the penis 9 (FIG. 3) which exceeds the space available in the corpus cavernosa which are located in the forward part 10 of the penis adjacent the glans penis 11, which amount of blood is, however, caused to flow from the abdomen 12 of the user into the penis by a "pumping" effect exerted by the lip portions on the arteries in the abdomen 12. A second inwardly directed protrusion 13 extends about the outer opening 3 and delimits the congestion space 8 on the outer end of the barrel wall 6.

Figure 3:
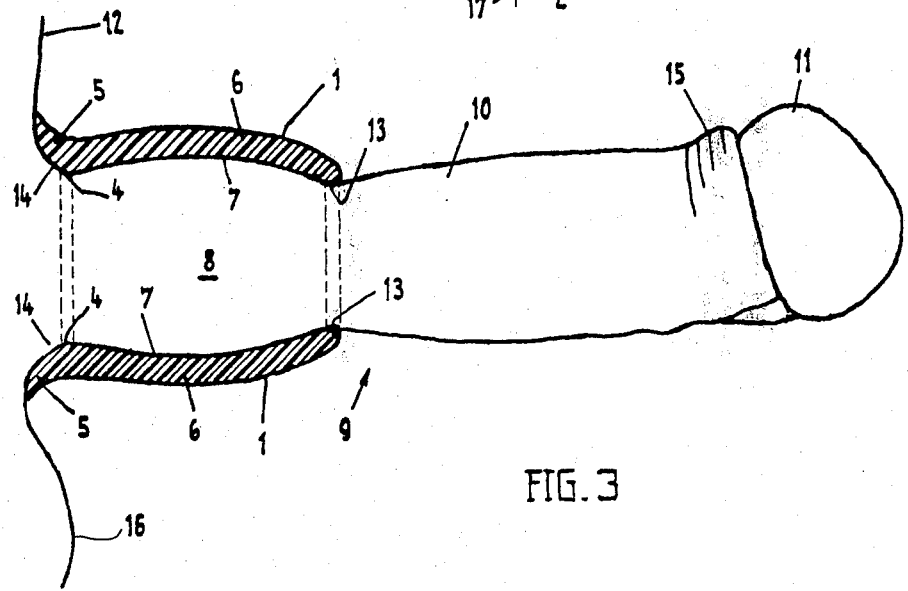
FIG. 3 shows an erected penis on which the embodiment of an erection holder shown in FIGS. 1 and 2 is mounted, the holder itself being shown in axial section.

The functioning of the erection holder according to the invention shall now be explained with reference to FIG. 3. It is advantageously greased on the internal sidewall 7 and pushed over the unerected, flaccid penis and moved, preferably, by a single pull or push, against the region of the abdomen surrounding the root 14 of the penis. Care must be taken, in doing so, that the skin of the penis is pulled forward so as to leave no folds thereof in the interior of the erection holder and to prevent the latter from sliding to and fro on the skin of the stiffened penis 9. The prepuce 15, if present, should be allowed to assume its natural position on the erected penis. The circumferential lip portion 5 should rest entirely on the abdomen 12 and against the scrotum 16, so that the inner protrusion 4 is in close vicinity to the penis root 14.

When the erection holder according to the invention has thus been mounted on the penis 9, each movement of the holder with, a corresponding movement of the penis 9, causes the lip portion 5 to tend to reassume its initial position, i.e. to make a closing movement toward the central longitudinal axis 17 of the holder (FIG. 2). Thereby, the blood present in the veins of the abdomen 12 and in the penis root 14 is urged into the lower, abdomen near the portion of the penis 9 inside the congestion space 8. The inner protrusion 4 then prevents this blood from flowing back unresisted out of the corpus cavernosa of the penis 9 back into the abdomen 12. This brings about a rapid erection of the penis 9 and renders its forward part 10 stiff. Once this has happened, the forward protrusion 13 of the erection holder, at the front end of the latter, prevents the blood now filling the corpus cavernosa in the front part 10 of penis 9 from flowing again toward the rear. The penis 9 thus remains in its erected state, even after ejaculation has taken place, when, without the presence of an erection holder, the corpus cavernosa will rapidly be emptied of blood, and the male partner loses his ability to continue the coitus, even if his female partner has not yet reached an orgasm.

When the erection holder according to the invention is correctly dimensioned and adapted approximately to the anatomical configuration of the penis to which it is to be applied, it will help even an impotent man who is not able to have a normal erection to achieve the erection and have a stiff penis. Thus, the holder according to the invention enables an otherwise normal man to maintain his penis in an erected state for several hours, and thus enable a fully satisfactory sexual intercourse of each man.

Moreover, the use of the erection holder according to the invention by the male partner also facilitates the attainment of an orgasm by the female partner as the outside wall 1 of the holder acts as a thickened portion of the penis and rubs against the female clitoris during the coitus.

Removal of the erection holder according to the invention from the penis 9 is easily achieved by pulling the prepuce 15, if present, over the glans penis 11 and then urging the penis 9, while still in the erected state, into the erection holder and preferably pulling the latter a short distance away from the abdomen 12. This will lead to a rapid slackening of the penis 9, whereupon the erection holder can be pulled off the penis 9 without difficulty.

In order to assist the beneficial effect of the erection holder according to the invention, the latter can be equipped with additional auxiliary means such as a scrotum band or an element especially designed for exciting the female partner, such elements being known per se.

Having thus described the preferred embodiment of the invention it should be understood that numerous structural modifications and adaptations may be resorted to without departing from the spirit of the invention.

What is claimed is:

1. An erection holder destined as an auxiliary means for enabling or prolonging an erection of the penis of a man, which holder is of sleeve-like configuration and consists of an elastic material of determined extensibility, said holder comprising a body having an outer sleeve wall surface, a hollow interior surrounded by an inner sleeve wall surface, a base end destined for coming to rest, during use, against a portion of the user's abdomen surrounding the root of his penis, and an outer end away from said base end, a first opening at said base end and a second opening, substantially opposite said first opening, at said outer end, a first inwardly directed protrusion surrounding said first opening, a circumferential tapered lip portion extending substantially axially relative to said body from adjacent said first protrusion, said lip portion being adapted to flex radially outward against the user's abdomen in the mounted position of the penis for cooperation with said first protrusion to pump blood from the abdomen into said penis, a second inwardly directed circumferential protrusion, spaced outwardly from said first protrusion, adjacent said outer end and surrounding said second opening, the wall portion of said holder intermediate said first and second protrusion being curved outwardly and said inner sleeve wall surface being concavely outwardly vaulted.

2. The erection holder of claim 1, wherein the cross sectional area of said first opening is larger than the cross sectional area of said second opening, and wherein the internal diameter of said first protrusion is larger than the internal diameter of said second protrusion.

3. The erection holder of claim 1, wherein the region thereof at the base end has a higher resistance to deformation than the region thereof at said outer end.

4. The erection holder of claim 1, wherein the intermediate region between said first and second protrusions is of less resistance to deformation than each of the regions thereof comprising said first and second protrusions.

5. The erection holder of claim 4, wherein said lip portion is integral with the remainder of the body of said holder.

6. The erection holder of claim 5, wherein said first protrusion has a blunt inwardly facing edge where said first protrusion merges with said lip portion.

7. The erection holder of claim 6, wherein the radius of the curvature of said first protrusion at said circumferential edge is from about 3 to 6 millimeters.

8. The erection holder of claim 6, wherein said intermediate region is barrel-shaped.

* * * * *